United States Patent [19]

Gayso

[11] 4,252,523
[45] Feb. 24, 1981

[54] APPARATUS AND METHOD FOR FORMING DENTAL MODELS

[75] Inventor: Donald W. Gayso, Memphis, Tenn.

[73] Assignee: Gayso Enterprises, Inc., Memphis, Tenn.

[21] Appl. No.: 961,468

[22] Filed: Nov. 14, 1978

[51] Int. Cl.³ .............................................. A61C 11/00
[52] U.S. Cl. .................................................... 433/60
[58] Field of Search ................. 32/32; 433/60, 61, 62, 433/63, 65, 58

[56] References Cited

U.S. PATENT DOCUMENTS

| 321,457 | 7/1885 | Smith | 433/65 |
| 1,815,956 | 7/1931 | Ralph | 433/58 |
| 2,365,475 | 12/1944 | Klein | 32/32 |
| 2,619,725 | 12/1952 | Roeser | 32/32 |
| 2,644,233 | 7/1953 | Shmukler et al. | 32/32 |
| 2,786,272 | 3/1957 | Lindly | 32/32 |
| 4,030,197 | 6/1977 | Linck et al. | 32/32 |

FOREIGN PATENT DOCUMENTS 2718863  8/1978  Fed. Rep. of Germany .............. 32/32

*Primary Examiner*—Gene Mancene
*Assistant Examiner*—John J. Wilson
*Attorney, Agent, or Firm*—Mason, Fenwick & Lawrence

[57] ABSTRACT

A dental model supporting articulator has an upper articulation tongue and a lower articulation tongue and pivotal means connecting the tongues to each other; first and second dental model mounting plastic slide members are removably mounted on the upper and lower articulation tongue members. Each slide member has retaining flanges and positioning means engageable with an articulation tongue member for insuring that the slide member is always accurately positioned in a single unchanging position on the tongue member; each slide also has anchor means engageable with a connecting mass of self-setting hardenable material in which the gum portion of a dental model is embedded so that upon hardening of the connecting mass the model supporting slide, the connecting mass and the model constitute a unitary structure which can be removed from the articulation tongue but can be returned to its original position on the articulation tongue.

7 Claims, 12 Drawing Figures

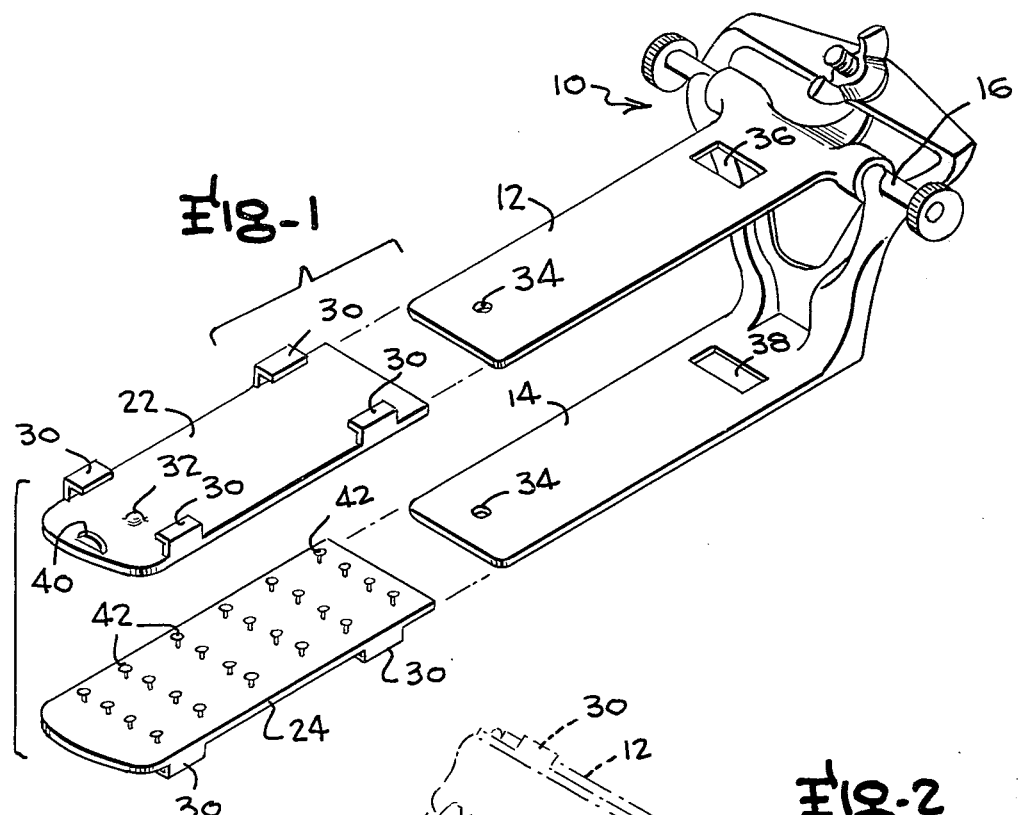
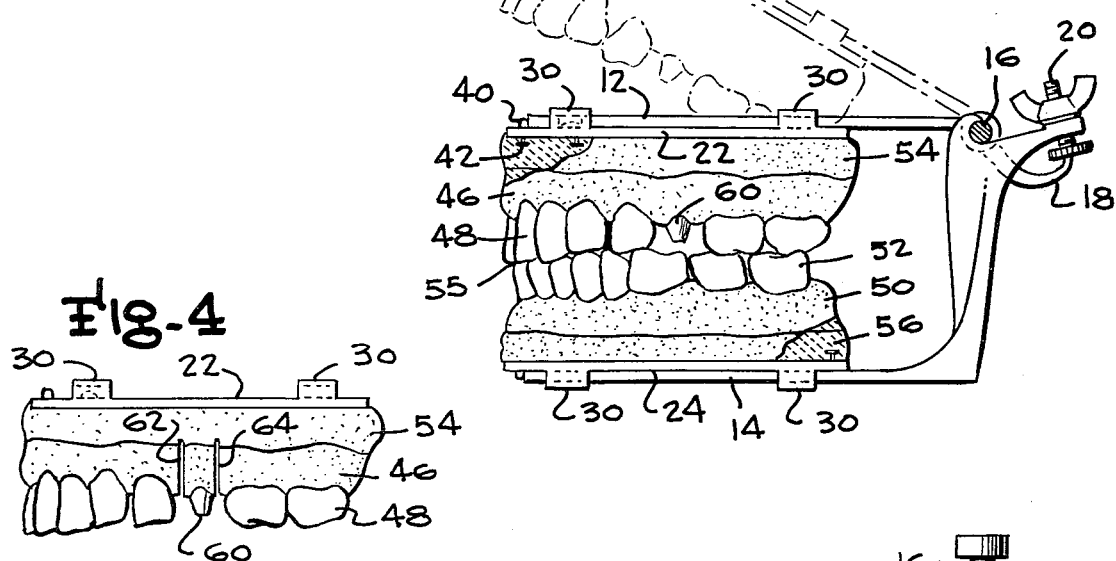
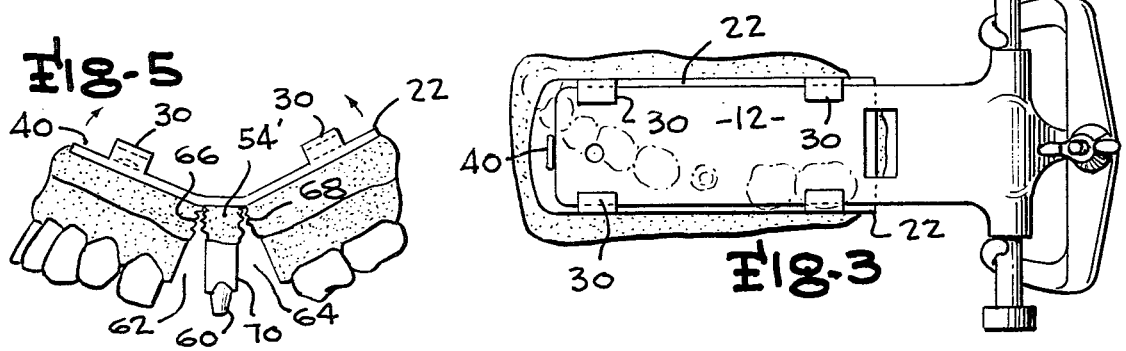

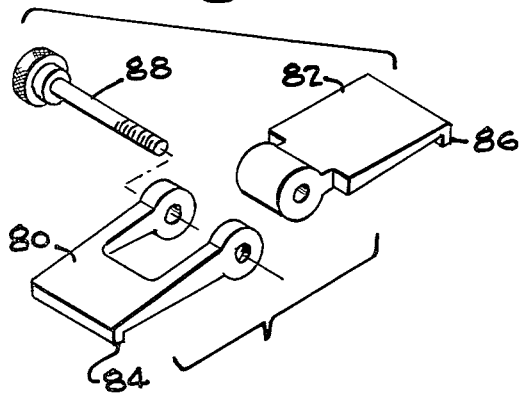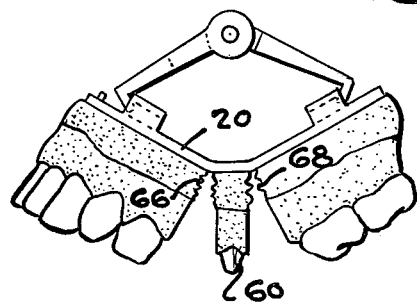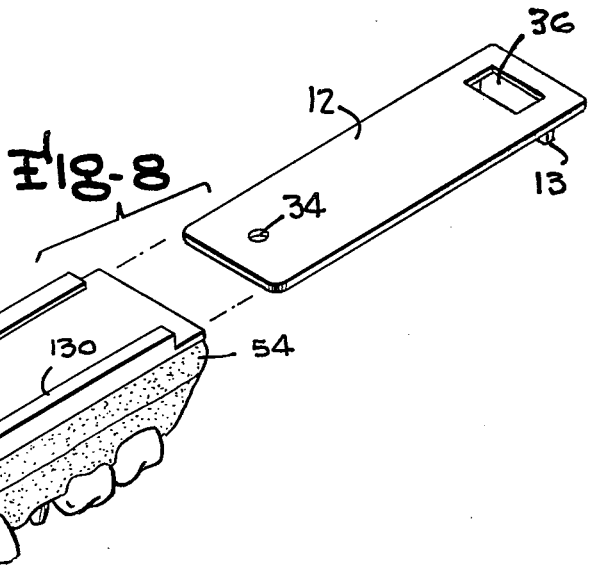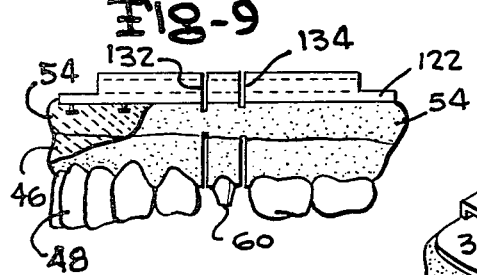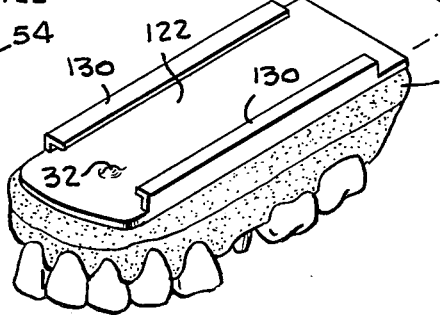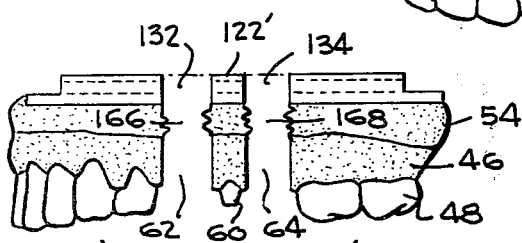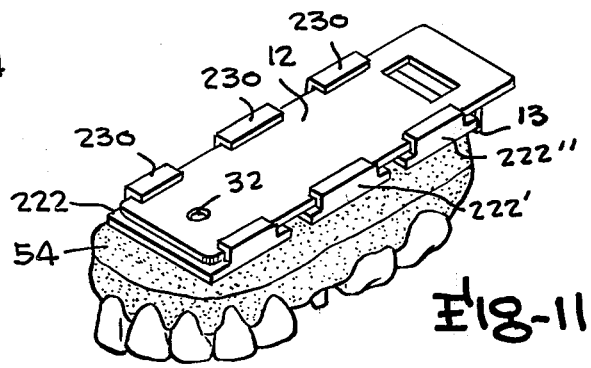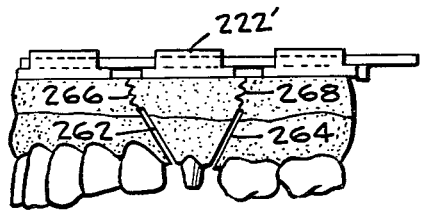

APPARATUS AND METHOD FOR FORMING DENTAL MODELS

This invention is in the field of dental apparatus and methods and is more specifically directed to an apparatus and method for use in the fabrication of dental prosthetic devices such as caps, crowns, bridges and the like. More specifically, the present invention is directed to a new and unique method and apparatus for forming a duplicate model of the dental structure of a person's mouth in which individual tooth elements and gum areas can be removed from the other components of the model to permit fabrication of prosthetic devices engageable with such tooth and gum areas.

In order to construct prosthetic dental devices such as crowns, caps, bridges and the like (which are hereinafter collectively referred to as "caps" for the sake of simplicity), it is necessary for the dentist to initially prepare a model of the patient's mouth by first taking impressions of the upper and lower teeth and adjacent gum areas. Casting material such as plaster of paris is then poured into the impressions to fill the areas defined in the impressions by the teeth and adjacent gums of the patient. Usually, the dentist simply makes the impressions of the patient's mouth with the prothesis fabrication being performed in a laboratory by a technician using the impressions prepared by the dentist. The dentist also prepares a bite impression of the upper teeth and the lower teeth formed of a relatively thin portion of impression material such as wax which is placed between the patient's teeth following which the patient closes his mouth to force his upper and lower teetl into the bite impression material to provide an accurate model of the alignment of the upper teeth with respect to the lower teeth.

When forming a cap, for example, the tooth to be capped is ground down to provide a tooth stub of relatively small size as compared to the original tooth and it has been the conventional practice in the past to insert a metal pin (or pins) in the casting material poured into the portion of the impression comprising the outline of the tooth stub and adjacent gum areas. This portion of the poured casting material is usually referred to as the "preparation" or the "prep" in that it represents the tooth for which the cap is to be prepared. A coating of vaseline is applied to the top surface of the casting around the area of the inserted pins and the remainder of the mould is filled with a foundation casting material permitted to set for a predetermined time for effecting hardening of the material.

After the casting material has hardened, it is separated from the mould and it is desired to separate the portion of the model (the prep) comprising the tooth stub from the remaining portions to permit the technician to use the tooth stub model for preparation of the cap or other contrivance to be fitted on the tooth stub. Such removal of the tooth stub model is effected by providing two relatively thin saw cuts through the model adjacent opposite sides of the tooth stub down to the foundation. Following such cutting, the prep can be manually removed from the foundation since the vaseline coating in the area around the pins prevents bonding to the foundation. Unfortunately, the coating of vaseline is not always complete and it is consequently impossible to separate the prep from the foundation components. One proposal for avoiding the foregoing problems has been to provide a metal pin having a radial metal shield extending outwardly from the pin to extend across the transverse area of the prep to permit separation of the tooth stub and surrounding gum area of the model from the foundation following cutting of the model downwardly through the gum portion of the model to the edges of the metal plate. Unfortunately, devices of the foregoing type do not provide satisfactory operation when the tooth is relatively thin due to the fact that the radial shield extending from the metal pin extends over into the model portions defining the teeth adjacent the tooth stub and it is consequently impossible to separate the small tooth stub portion of the model without destroying the adjacent model portions of the adjacent teeth.

Fabrication of the dental device also requires the positioning of the model of the upper teeth and the model of the lower teeth on an articulation support member comprising two articulation tongues pivoted together to provide articulation between the model of the upper teeth and the model of the lower teeth for effecting proper positioning and sizing of the cap or other member being fabricated. Such connection of the models to the articulation members is effected by providing a mounting for each model consisting of a quantity of unhardened plaster of paris or the like provided on each articulation tongue following which the foundation of each model is pressed therein. The bite impression is positioned between the upper and lower teeth models which are maneuvered into proper alignment therewith following which the mounting mass on each of the tongue members of the articulation member is permitted to harden to provide a fixed connection between the properly aligned models and the articulation member. The prep can then be removed from the model for use by the technician and reinserted in the model as required during the fabrication of the cap. Upon completion of the cap being fabricated, the only way in which the model can be removed from the articulation member is to break the mounting mass of hardened plaster of paris on the slotted tongues of the articulation member. Once the foregoing has been accomplished, it is impossible to reposition the components on the articulation member and it is consequently essentially impossible for the dentist to check the accuracy of the technician's work.

Another approach is essentially identical to the foregoing except that a casting block that can be disassembled is used with the foundation component being first trimmed down for size and then embedded in the casting block. The casting block and the associated model is then attached to the articulation tongue by embedding in a quantity of plaster of paris on the tongue in a manner similar to the method in which the foundation assembly is directly embedded in the plaster of paris on the articulation tongue. When using such trays, the tray is disassembled and the model and the foundation component are cut on opposite sides of the tooth on which the cap is to be provided so as to permit removal of the formed prep.

Therefore, it is the primary object of this invention to provide a new and improved apparatus and method for forming dental models for use in the preparation of prosthetic dental devices such as caps, crowns, bridges and the like.

Achievement of the object of this invention is enabled through the preferred embodiment for its practice in which separation of the prep from the other model components is easily achieved with both the upper and lower models being easily removed from the articulation means but being replaceable thereon in exact aligned manner, as opposed to prior practices in which such removal and replacement is not possible, for checking the accuracy of the work. It is consequently possible for the dentist to position the upper and lower models on his own articulator following return of the completed dental device from the laboratory to enable confirmation that the device is properly made. A further advantage arises in the fact that the subject invention does not require the use of pins associated with the prep and consequently avoids the cost of such.

More specifically, the preferred embodiment comprises an articulation member having first and second generally rectangular articulation tongues having a conventional hinged connection permitting the upper tongue to pivot with respect to the lower tongue and vice versa. Each of the articulation tongues has a slidably mounted model mounting slide plate having retaining flanges extending up and over the side edges of the tongue and permitting the removable mounting of the model mounting plate on the tongue. Additionally, each of the articulation tongues includes a positioning aperture into which a lug on the slide plate is received for always insuring accurate positioning the slide plate on the tongue in the same position. The side of each slide plate opposite the side engaged with its supporting articulation tongue is provided with a plurality of outwardly extending model anchor members in the form of protrusions shaped generally in the shape of a cylindrical member having an enlarged head portion. In use, the upper model mounting slide plate is positioned on the upper articulation tongue with the lower model mounting slide plate being positioned on the lower articulation tongue and a quantity of plaster of paris comprising a model mounting mass is positioned on the anchor members on each of the plates. The model of the lower teeth is positioned in the mounting mass on the lower plate with the model of the upper teeth being positioned in the mounting mass extending downwardly from the lower surface of the upper plate. The bite impression is positioned between the upper and lower models and the models are maneuvered to bring them into proper alignment as dictated by the configuration of the bite impression. After the mounting masses have hardened, either the upper model or the lower model can be removed from the articulation means by a simple sliding movement of its supporting plate from its associated articulation tongue. However, unlike the previous devices, the upper and lower models can be repositioned on the articulation device or on a like articulation device by simply repositioning its supporting plate on the proper tongue of such an articulation device.

Another aspect of the invention resides in the fact that each of the articulation plates is made of flexible plastic material capable of being bent. Thus, when forming a cap, the particular model is removed from the articulation means and is cut downwardly through the model and the foundation toward but not completely to the support plate along two cut lines on opposite sides of the tooth stub. The support plate is then simply bent backwardly so that remaining uncut plaster portions break apart on opposite sides of the tooth stub and are bent away from the tooth stub which is then clear for use by the technician. The tooth stub can simply remain attached to the plate if desired or it can be removed from the supporting plate if the technician deems such removal necessary.

A better understanding of the nature and operation of the subject invention will be achieved when the following detailed description is considered in conjunction with the appended drawings, in which:

FIG. 1 comprises an exploded perspective view of the articulator and its associated upper and lower model mounting slide plates;

FIG. 2 is a side elevation view of the articulator of FIG. 2 illustrating it in use with the model mounting slide plates positioned on the articulator tongue and supporting an upper tooth model and a lower tooth model;

FIG. 3 is a plan view of the articulator of FIG. 2;

FIG. 4 is a side elevational view of an upper tooth model mounted on its slide support plate and illustrating an initial step in the modification of the model to permit isolation of the prep from the adjacent model components;

FIG. 5 is similar to FIG. 4 but illustrates the parts in a subsequent position of orientation achieved during practice of the inventive method;

FIG. 6 is an exploded perspective view of a model holding device for use with an associated model and model support plate;

FIG. 7 is an elevational view of the model holding device of FIG. 6 as used in conjunction with an associated model and its model mounting slide plate;

FIG. 8 is a perspective view of another embodiment of the model mounting slide plate as associated with an articulation FIG. 9 is a side elevation view illustrating an initial step in the use of the model and associated support plate of FIG. 8;

FIG. 10 is a side elevation view illustrating a subsequent operation in the use of the embodiment of FIGS. 8 and 9;

FIG. 11 is a perspective view of a third embodiment of the support slide plate; and FIG. 12 is a side elevation view of the embodiment of FIG. 11 illustrating an initial step in the use thereof.

Attention is initially invited to FIG. 1 of the drawings which illustrates articulation means, generally designated 10, having an upper articulation tongue 12 and a lower articulation tongue 14 with the upper tongue 12 being mounted for hinged pivotal movement about a pivot shaft 16 and having a rearwardly extending positioning lug 18 engageable with the lower end of an adjustment screw 20 the position of which determines the extent to which the upper tongue 12 can be pivoted in a counterclockwise direction as shown in FIG. 2. Articulator 12 is completely conventional with the exception of the fact that the upper tongue 12 and the lower tongue 14 are of unique construction for respectively permitting the removable positioning of an upper model mounting slide 22 and a lower model mounting slide 24 thereon. The unique construction of the upper and lower tongues and the slides 22 and 24 permits models of the upper and lower teeth of a patient to be removably positioned on the articulator in a manner for a purpose which will become apparent. The upper and lower slides 22 and 24 are of identical plastic construction with each essentially consisting of a flat plate having side edges with each side edge including two right angle flange members 30 adapted to slide over the respective side edges of their respective articulation tongue. Additionally, each of the slides includes a positioning dimple 32 matingly engageable with a positioning recess 34 in each of the articulation tongues. Consequently, each of the model mounting slide plates 22, 24 can always be positioned in exactly the same position on its respective articulation tongue. Additionally, the tongues 12 and 14 include apertures 36 and 38 respectively for permitting each engagement of the ends of the model mounting slide plates such as by a screw driver or the like for initiating removal of a particular slide plate from its associated articulation tongue. A lug stop 40 is also provided on the model mounting slide plates 22 and 24 for limiting the amount of inward movement of the slide plate on its respective supporting articulation tongue as best shown in FIG. 2. Lastly, each of the slide plates includes a plurality of model anchor members 42 for permitting the mounting of the models on the respective slide plates in a manner to be discussed.

A typical usage of the foregoing articulator and model mounting slide plate will now be discussed with it being understood that upper and lower models of the patient's mouth are provided in a conventional manner with the upper model consisting of a gum portion 46 and a tooth portion 48 and the lower model similarly including a gum portion 50 and tooth portion 52 as best shown in FIG. 2. The upper model is attached to the upper model mounting slide 22 by initially positioning a mass 54 of unhardened plaster of paris on the lower surface of the plate 22 over the anchoring members 42 following which the gum portion 46 of the upper model is pressed into the unhardened mass 54. Similarly, another unhardened mass of plastic of paris 56 is provided on the upper surface of the lower model mounting slide 24 and the gum portion 50 of the lower model is pressed into this unhardened mass. It should be understood that the slides are positioned on the respective articulation tongues 12 and 14 prior to the foregoing operation and the bite impression 55 is positioned between the upper and lower models which are maneuvered and manipulated while the masses 54 and 56 remain unhardened to achieve proper alignment of the upper and lower models with respect to each other. Upon achievement of such proper alignment, the masses 54 and 56 of plaster of paris are permitted to harden to provide a fixed connection thereto between each mass and its respective model and its respective model mounting slide by virtue of the engagement of the anchor members 42. Following hardening of the plaster of paris masses 54 and 56, the articulator can be operated by pivoting the upper tongue 12 about pin 16.

In the illustrated example, the upper model includes a tooth stub 60 for which a cap is to be prepared. Consequently, it is desirable to isolate the tooth stub to provide a prep for preparation of the necessary cap. Such isolation is accomplished by initially removing the upper model mounting slide 22 from the upper articulation tongue 12 and cutting along cut lines 62 and 64 along opposite sides of the tooth stub as shown in FIG. 4. It should be noted that the saw cuts 62 and 64 extend into but not through the mounting mass 54. The upper model mounting slide plate 22 is then bent backwardly as shown in FIG. 5 to provide a break in the mounting mass in the areas 66 and 68 to isolate the tooth stub 60 and provide a prep consisting of the stub 60, gum portions 70 and portion 54' of the mounting mass 54.

The technician can permit the prep to remain in position on the slide 22 in the manner illustrated in FIG. 7 with the slide being held in its rearwardly bent position to provide access to the prep by the use of a holding means consisting of pivotal clamp plates 80, 82, respectively, having holding flanges 84 and 86 engageable with the flanges 30 on the back side of the slide 22. Screw means 88 provides pivotal adjustment between the elements 80 and 82 and permits them to be clamped in any desired position for holding the model mounting slide 22 in any desired adjusted position.

FIGS. 8, 9 and 10 illustrate a second embodiment which differs from the first embodiment solely in that a retaining flange 130 is provided to extend substantially along the entire side edge of the plate 122. In this embodiment, it is not necessary for the model mounting slide 122 to be formed of flexible material. Separation of the prep from the other components is achieved by providing saw cut lines at areas 62 and 64 as in the first embodiment and by further providing saw cut lines 132 and 134 through the model mounting slide plate 122 as shown in FIG. 9. Consequently, the mounting mass 54 provides the only remaining connection of the components and this mass is broken in areas 166 and 168 which are analagous to areas 66 and 68 of the first embodiment. The prep resultant from such breaking operation consequently includes a portion 122' of the slide 122. The break edges defined by areas 166 and 168 permit the entire assembly to be repositioned accurately in its original position on the articulation tongue 12 if desired. An additional manner in which the embodiment of FIGS. 8 through 10 differs from the previous embodiments is that a stop lug 13 is provided on the tongue 12 for limiting inward movement of the model mounting slide plates 122.

FIGS. 11 and 12 illustrate a further alternative embodiment in which an articulation tongue identical to the tongue of FIGS. 8 through 10 receives a second alternative model mounting arrangement consisting of three small slide assemblies 222, 222' and 222" each having retaining flanges 230 along opposite edges fitted over the tongue as shown in FIG. 11. The individual small model mounting slides are positioned as desired in accordance with the requirements of the particular model with it being understood that each of the smaller slides includes downwardly extending anchor members identical to members 42 of the previously discussed embodiments. The model is attached to the plural slides by a mass 54 of plaster of paris in the same manner as the previously discussed models and upon hardening of the mass 54 is ready for subsequent usage. The inward slide 222" is engaged with the stop lug 13 as shown in FIG. 11 and upon removal of the model unit from the tongue, saw cuts are provided through the gum area along lines 262 and 264 and the mass 54 is broken in areas 266 and 268 to separate the prep components which includes the middle slide 222' as shown in FIG. 12. The entire assembly can be repositioned in its original position on the tongue if desired. The outermost slide 222 includes a positioning dimple 32 for engagement with the opening 34 in the slide to effect the required positioning. Consequently, the prep is separable from the remaining portions of the model but they can be reconnected in their original position on the tongue if desired. The broken areas defined in portions 266 and 268 permit an accurate repositioning of the prep with respect to the other model components.

Additionally, numerous modifications of the foregoing embodiments will undoubtedly occur to those of skill in the art. For example, while the illustrated embodiments disclose articulators and model supporting slides capable of supporting a model of only one side of the patient's mouth, it should be understood that wider articulators and wider model supporting slides could be employed for supporting upper and lower models of a person's entire dental structure. Similarly, it would be possible to employ pairs of side-by-side upper tongue members in conjunction with pairs of side-by-side lower tongue members for the same purpose. In which case, the upper pair of tongue members would receive two of the model supporting slides of the type disclosed in FIGS. 1, 8, 11 etc., while the lower pair would similarly receive two of the model support slides with the two upper slides serving to provide a mounting for the model of the complete dental structure of the patient's upper and lower dental areas. In such a construction, it would be possible to separate the right and left portions of the model by simply sawing along a medial line between the two adjacent model support slides. Also, it should be understood that other stop members, such as metal plates or the like, could be attached to the slides for effecting uniform positioning of the slides with respect to their associated articulation tongue members. Additionally, it would be possible in some cases to dispense with the use of the slides by directly positioning the holding mass 54 or 56 on tapered smooth surfaced articulation tongue members formed of plastic or other material to which the casing material will not adhere. Such tongue members would taper downwardly from their hinge end toward their outer end.

I claim:

1. A support assembly for supporting dental models comprising an articulator having an upper articulation tongue and a lower articulation tongue pivotally connected to each other, first and second elongated model mounting slide members formed of flexible plastic material of sufficient flexibility to permit manual bending thereof and adapted to be removably mounted on said upper and lower articulation tongue members by sliding linear movement thereon, each of said model mounting slide members having positioning means alignable with positioning means on said articulation tongue members by linear movement of the slide member on the associated tongue member for insuring that said slide members are always accurately positioned in a single unchanging position on an articulation tongue member, each of said model mounting slides further including anchor means engageable with a connecting mass of self-setting hardenable material in which the gum portion of a dental model is embedded so that upon hardening of the connecting mass, the model supporting slide, the connecting mass and the model constitute a unitary structure which can be removed from the articulation tongue on which it is mounted by linear sliding movement thereon for work by a technician but can be returned to its original position on one of the articulation tongue means for permitting comparison with the model of a similar unitary structure on the other articulation tongue means.

2. A method of providing a working model of a dental patient's mouth, said method comprising the steps of providing a hardened model of upper teeth and gum areas of the patient and a model of the lower teeth and gum areas of the patient, providing a mass of unhardened hardenable mounting material on a slide means removably mounted on an upper articulation tongue of an articulator, providing a second mass of unhardened hardenable material on slide means removably mounted on a lower articulation tongue of an articulator, manipulating said upper and lower models to align them with each other in the same alignment they have in the patient's mouth, permitting said hardenable material to set and become hard, removing one of said slide members from its articulation tongue and partially cutting through the gum portion of the model on the removed slide member along cut lines on opposite sides of a prep tooth, and bending the removed slide and adjacent model portions backwardly to break away the adjacent model portions and mounting material along break lines extending from the inner extent of said cut lines to the removed slide means to provide work clearance adjacent the prep tooth to provide access to the prep tooth for the purpose of fabricating a dental prosthetic device therefor.

3. A model mounting slide member of unitary construction including a flexible and manually bendable plastic plate portion, side clamp portions along opposite edges of said plate portion dimensioned and shaped to be fittable over and supported on an elongated support means with one side of the flat plate portion engaged with the elongated support means and anchor means comprising a plurality of protrusions extending outwardly from the other side of said flat plate portion.

4. The invention of claim 3 wherein said side clamp portions comprise flange members unitarily extending from opposite edge surfaces of said flat plate portion.

5. The invention of claim 4 additionally including an outwardly extending positioning dimple member on said flat plate portion.

6. A method of providing a working model of a dental patient's mouth, said method comprising the steps of providing a hardened model of upper teeth and gum areas of the patient and a model of the lower teeth and gum areas of the patient, providng a mass of unhardened hardenable mounting material on a slide means removably mounted on an upper articulation tongue of an articulator, providing a second mass of unhardened hardenable material on slide means removably mounted on a lower articulation tongue of an articulator, manipulating said upper and lower models to align them with each other in the same alignment they have in the patient's mouth, permitting said hardenable material to set and become hard, removing one of said slide members from its articulation tongue, partially cutting through the gum portion of the model on the removed slide member along cut lines on opposite sides of a prep tooth, and cutting through the removed slide in two areas in general alignment with the cuts made in the gum portion of the model while leaving a thickness of the mounting material between the cuts and breaking said thickness of mounting material along break lines extending from the inner extent of said first made cut line to the inner extent of said second made cut lines to provide separation of the prep tooth from the other model components for the purpose of providing access to the prep tooth for permitting the fabrication of a dental prosthetic device therefor.

7. A method of providing a working model of a dental patient's mouth, said method comprising the steps of providing a hardened model of upper teeth and gum areas of the patient and a model of the lower teeth and gum areas of the patient, providing a mass of unhardened hardenable mounting material on a slide means removably mounted on an upper articulation tongue of an articulator, providing a second mass of unhardened hardenable material on slide means removably mounted on a lower articulation tongue of an articulator, manipulating said upper and lower models to align them with each other in the same alignment they have in the patient's mouth, permitting said hardenable material to set and become hard, removing one of said slide members from its articulation tongue, cutting through the gum portion of the model on the removed slide member along cut lines on opposite sides of a prep tooth, and bending the removed slide means and adjacent model portions backwardly to break away the adjacent model portions and mounting material along break lines extending from the inner extent of said cut lines to effect separation of the prep tooth from the other components to provide access to the prep tooth for permitting the fabrication of a dental prosthetic device therefor.

* * * * *